United States Patent
Khanna

(10) Patent No.: US 12,268,448 B1
(45) Date of Patent: Apr. 8, 2025

(54) OPHTHALMIC APPARATUS AND SYSTEMS FOR TELE-OPHTHALMOLOGY AND COLLABORATIVE CARE

(71) Applicant: Sandeep Khanna, Los Angeles, CA (US)

(72) Inventor: Sandeep Khanna, Los Angeles, CA (US)

( * ) Notice: Subject to any disclaimer, the term of this patent is extended or adjusted under 35 U.S.C. 154(b) by 707 days.

(21) Appl. No.: 17/360,785

(22) Filed: Jun. 28, 2021

Related U.S. Application Data

(60) Provisional application No. 63/044,502, filed on Jun. 26, 2020.

(51) Int. Cl.
| | |
|---|---|
| *A61B 3/10* | (2006.01) |
| *A61B 3/00* | (2006.01) |
| *A61B 3/135* | (2006.01) |
| *A61B 3/14* | (2006.01) |
| *G16H 40/67* | (2018.01) |
| *G16H 80/00* | (2018.01) |

(52) U.S. Cl.
CPC ............ *A61B 3/135* (2013.01); *A61B 3/0008* (2013.01); *A61B 3/0041* (2013.01); *A61B 3/14* (2013.01); *G16H 40/67* (2018.01); *G16H 80/00* (2018.01)

(58) Field of Classification Search
CPC ..... A61B 3/135; A61B 3/0008; A61B 3/0041; A61B 3/14; G16H 40/67; G16H 40/00
USPC ......................................... 351/206, 214, 221
See application file for complete search history.

(56) References Cited

U.S. PATENT DOCUMENTS

| | | | | |
|---|---|---|---|---|
| 7,325,923 | B2 * | 2/2008 | Makino | G16H 40/67 |
| | | | | 351/200 |
| 2003/0117580 | A1 * | 6/2003 | Franz | G16H 50/20 |
| | | | | 351/205 |
| 2017/0076043 | A1 * | 3/2017 | Dormer | G16H 40/67 |
| 2018/0220889 | A1 * | 8/2018 | Dirghangi | A61B 3/156 |
| 2019/0110753 | A1 * | 4/2019 | Zhang | G16H 50/20 |

FOREIGN PATENT DOCUMENTS

| | | | | |
|---|---|---|---|---|
| WO | WO-2018013923 A1 * | 1/2018 | | A61B 3/028 |
| WO | WO-2020180729 A1 * | 9/2020 | | A61B 3/0016 |

* cited by examiner

*Primary Examiner* — Mahidere S Sahle
(74) *Attorney, Agent, or Firm* — Plager Schack LLP; Mark H. Plager; Alexis Saenz

(57) ABSTRACT

The proposed technology includes ophthalmic apparatuses and systems that allow transmission of a digital slit-lamp output (both of the visible light as well as of infra-red wavelength) over the web in "real-time" alongside face-to-face audio-visual communication between the various parties. The digital output of the camera will be in a format that is compatible with direct transmission over the web. This allows a person(s) at the remote site to see the slit-lamp imagery as if the remote examiner(s) were on site in the presence of the patient and simultaneously video-chat with the operator of the microscope to provide tele-consultation. The features also facilitate collaborative care between several providers, as well as patient representative(s), by enhancing the audio-visual communication between parties with the actual slit lamp imagery of the patient in real time.

20 Claims, 16 Drawing Sheets

OPHTHALMIC APPARATUS AND SYSTEMS FOR TELE-OPHTHALMOLOGY AND COLLABORATIVE CARE

CROSS-REFERENCE TO RELATED APPLICATION

This application claims priority to provisional patent application U.S. Ser. No. 63/044,502 filed on Jun. 26, 2020, the entire contents of which, including drawings and a specification are herein incorporated by reference.

BACKGROUND

The embodiments herein relate generally to ophthalmic systems and in particular, to an ophthalmic apparatus and system for tele-ophthalmology and collaborative care.

Tele-ophthalmology, in its current form, is either a face-to-face video consultation between a patient and the consulting eye care provider using a web-based software in Protected Health Information (PHI) format, or involves some form of an asynchronous store-and-forward (SAF) telecommunications technique to facilitate communication between two providers (SAF provider-to-provider tele-consults) using the acquired images or recorded videos from various ophthalmic devices like slit lamp microscope.

Aforementioned uses of Tele-ophthalmology have rarely addressed "real-time" remote slit-lamp examination by an eyecare provider (RT provider-to-provider tele-consults). The use of digital slit lamps in tele-ophthalmology have invariably involved SAF-technique using stored images or recorded videos using a tele-communication technique in an asynchronous fashion, but rarely with direct feed from the slit-lamp being transmitted to a consulting provider in real-time and in a Protected Health Information (PHI) format (like with HIPAA-compliance). In the rare instances, in which the ophthalmic systems were devised to allow remote diagnosis with real-time slit-lamp data, it was unaccompanied by concomitant audio-visual communication between the participants or were in a format that were not specified to protect patient health information. In addition, the digital output of the camera will be in a format that is compatible with direct transmission over the web without any data conversion or data storage.

SUMMARY

In one aspect of the subject technology, an ophthalmic system for tele-ophthalmology and collaborative care is disclosed. The system comprises: a slit lamp configured to capture an image of an eye of a patient; a digital camera coupled to the slit lamp and positioned to capture imagery from the light output of the beam splitter; a video adapter coupled to the slit lamp to focus a light output from the slit lamp to the attached digital camera; a communications cable connected between the digital camera and a first computing device, to forward the captured imagery to the first computing device; and a network connection configured to transmit the captured imagery from the first computing device to a remote computing device(s) connected wirelessly to the first computing device, wherein the transmitted captured imagery is seen in real-time as if remote user(s) at the remote computing device(s) were seeing the image of the eye of the patient on site in the presence of the patient.

In another aspect, a method of performing a tele-ophthalmological examination on a patient is disclosed. The method comprises: capturing light reflected off a patient's eye using a slit lamp in a first location; splitting the reflected light from the patient's eye in the slit lamp; diverting a portion of the split reflected light into a digital camera; converting the reflected light diverted to the digital camera into a digital format of data; transmitting the digitally formatted data through a network to a remote computing device located in a second location; and displaying an image of the patient's eye in real-time video on the remote computing device.

In still yet another aspect, a computer program product for hosting tele-ophthalmological examination is disclosed. The computer program product comprises a non-transitory computer readable storage medium having computer readable program code embodied therewith. The computer readable program code is configured to, when executed by a processor, to: capture light reflected off a patient's eye using a slit lamp in a first location; split the reflected light from the patient's eye in the slit lamp; divert a portion of the split reflected light into a digital camera; convert the reflected light diverted to the digital camera into a digital format of data; transmit the digitally formatted data through a network to a remote computing device located in a second location; and display an image of the patient's eye in real-time video on the remote computing device.

BRIEF DESCRIPTION OF THE FIGURES

The detailed description of some embodiments of the invention is made below with reference to the accompanying figures.

DETAILED DESCRIPTION OF CERTAIN EMBODIMENTS

In general, and referring to the Figures, embodiments of the disclosed subject technology provide an ophthalmological test whose result may be viewed simultaneously by various participants, some of which may be remotely located from the ophthalmological test device's location. In an exemplary embodiment, a digital slit-lamp may be interfaced with several web-based software platforms (for example, WebRTC) to allow an observer to view the slit-lamp examination imagery being conducted at a remote location in "real time" seamlessly and alongside "face-to-face" video chat. The image data from a slit-lamp is transmitted in a format that streams the data in real-time as if the remote user/viewer were seeing the slit-lamp imagery on site in the presence of the patient.

Furthermore, embodiments will facilitate collaborative care between several providers, as well as patient representative(s), by enhancing the video chat between parties with the actual slit lamp imagery of the patient in real time.

Figure 1:
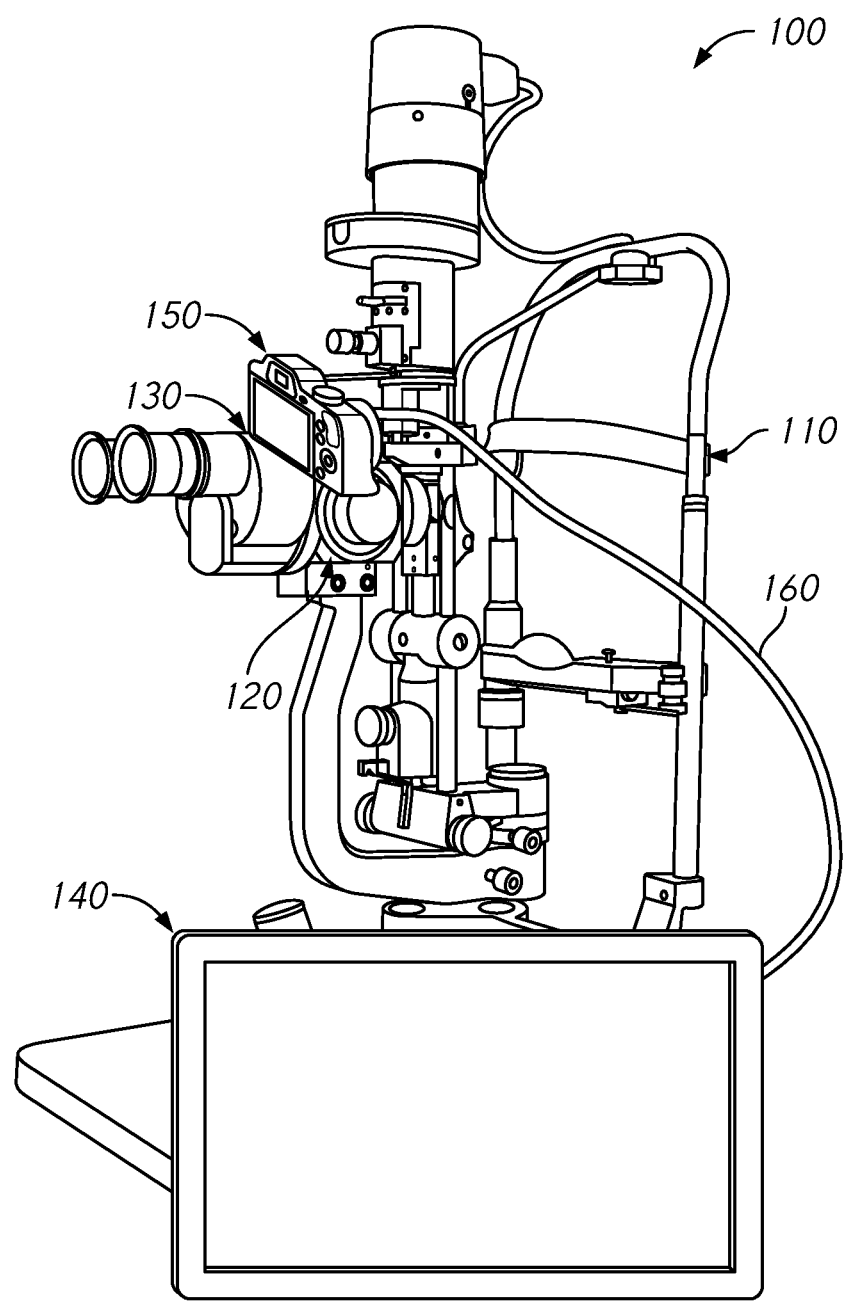
FIG. 1 is a perspective view of an operator side of an ophthalmic system for tele-ophthalmology and collaborative care in accordance with embodiments of the subject technology.

Referring now to FIG. 1, a system 100 may include a slit lamp microscope 110, which as will be appreciated, is a key tool in determining the health of the eyes and detecting eye disease. The system 100 may further include a digital camera 150 connected to the slit lamp 110 to allow image capture or video recording of the eye during an examination. To permit tele-consults using the data captured, the current paradigm may use an asynchronous store-and-forward (SAF) technique to allow tele-consults.

The ophthalmic apparatus and systems allow digital output from the slit lamp 110 (both of the visible light as well as of the infra-red wavelength) to be transmitted over the web in "real-time" alongside face-to-face audio-visual communication between the various parties. This allows:

1) person(s) at the remote site to see the slit-lamp imagery as if the remote examiner(s)/viewers was/were on site in the presence of the patient and simultaneously allow video-chat with the operator of the microscope to provide teleconsultation, and
2) facilitate collaborative care between several providers, as well as patient representative(s), by enhancing the audio-visual communication between parties with the actual slit lamp imagery of the patient shown in real time.

The system 100 may generally be configured in a network embodiment that includes an operator side and a remote examiner side. The operator side of the system is shown according to an exemplary embodiment in FIG. 1. The operator-side of the network comprises the slit lamp 110, a beam-splitter 120, a video-adapter 130, a first computing device 140 for the operator of the slit lamp microscope 110, a digital camera 150 (that may include a feature to toggle to allow capture of both the color as well as infra-red imagery), and a communication cord 160, (which may be for example, a USB format cable). In some embodiments, software for the operator of the microscope and a media server 8 (FIG. 2) connected to the system 100 via a telecommunications connection may be included.

Figure 2:
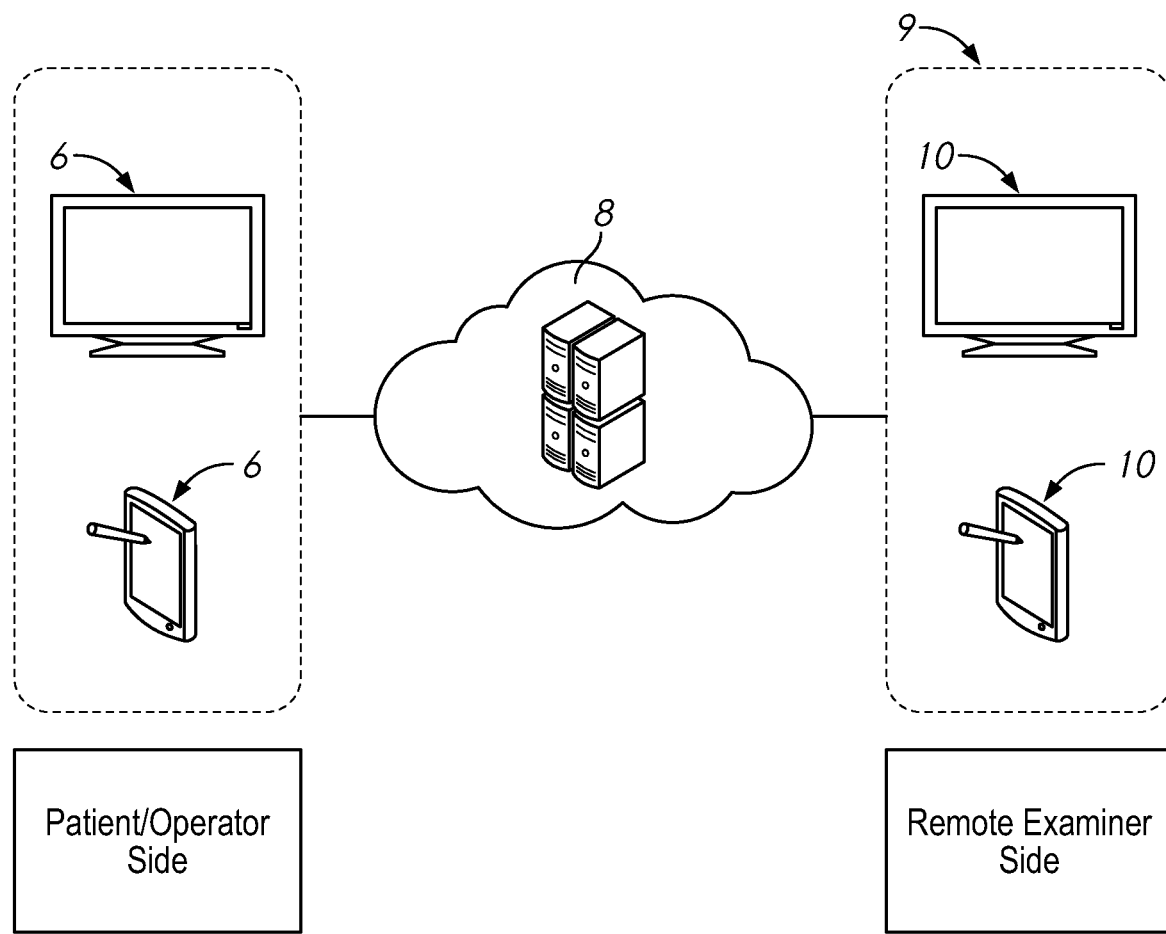
FIG. 2 is a block diagram an ophthalmic system for tele-ophthalmology and collaborative care showing both the operator side and remote examiner(s) side connected through a network in accordance with embodiments of the subject technology.

For example, and referring to FIG. 2, a network embodiment is shown connecting the patient/operator side to a remote examiner side via media server 8 through a telecommunications network. On the remote examiner side of the network, the system includes one or more computing device(s) 9, which may be for use by the remote examiner(s). The computing device(s) 9 may include a copy of the software 10 (which may be the same as software 6 or a tailored version of software just for remote examiner(s)) which may be configured with an interface and features for the remote examiner(s).

In an exemplary embodiment, the slit lamp 110 may be modified to allow insertion of the beam splitter 120 with an integrated video adapter 130 attached. This allows the video-adapter 130 to focus the light output from the slit lamp 110 to the attached digital camera 150. The digital camera 150 will both receive the power as well as transmit imagery through an attached cable 160 to the computing device 140.

Figure 3:
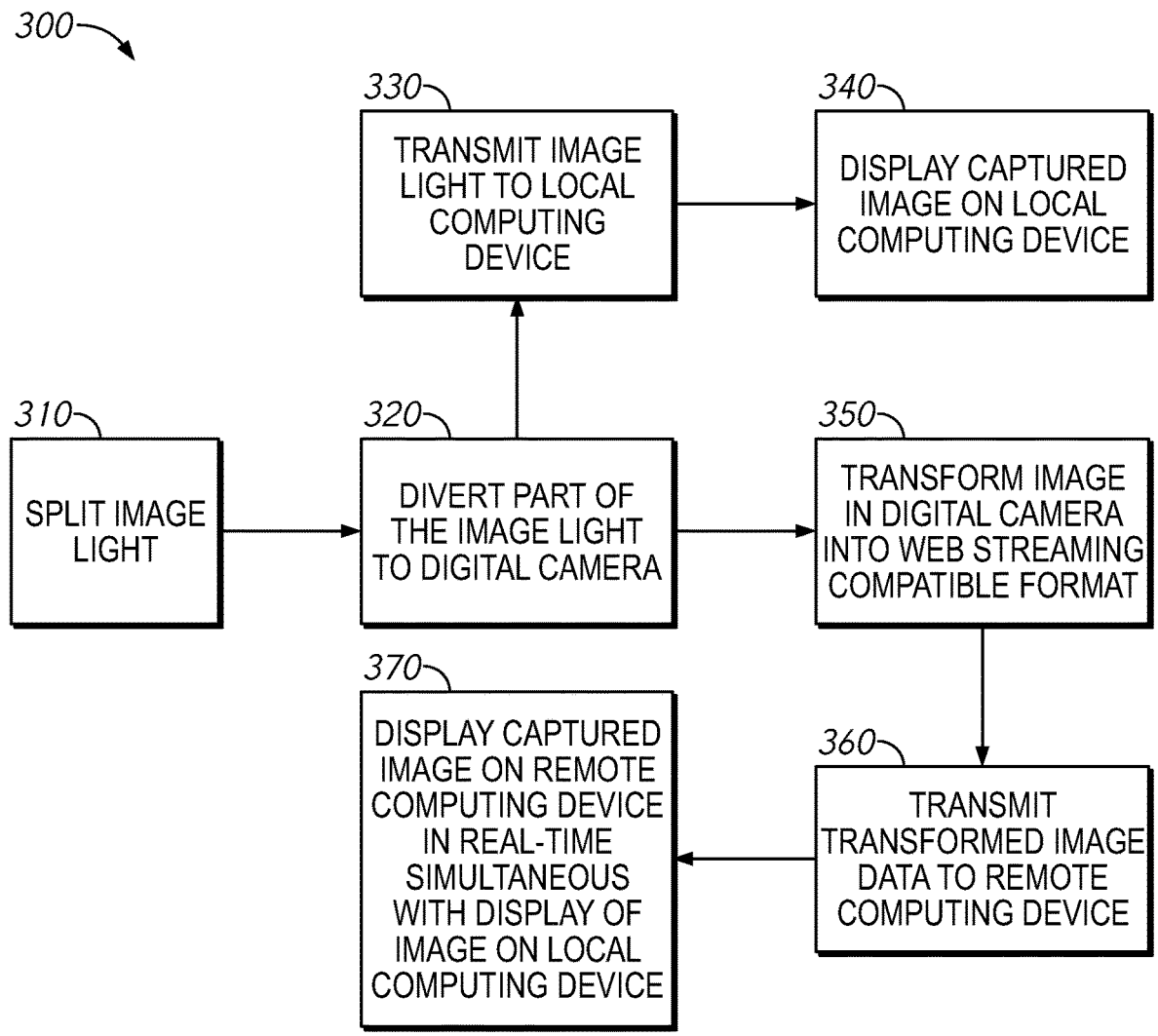
FIG. 3 is a flowchart of a method of generating simultaneous tele-ophthalmological imaging to remote locations in accordance with embodiments of the subject technology.

Referring now to FIG. 3, a method 300 of generating simultaneous tele-ophthalmological imaging to remote locations is shown according to an exemplary embodiment. The image light may be split 310 as the image is captured in the system. The captured light from the slit lamp may be partially diverted 320 through the beam splitter.

Some of the diverted image light may be sent 330 to the local computing device (thus, still allowing simultaneous actual examination by the local user/operator). The captured image may be displayed 340 on the local computing device.

The other diverted portion of the image may be directed to the video adapter to focus the image onto the digital camera. At the digital camera, the image may be transformed 350 into a web streaming compatible format. The communication cable supplies the electrical power to the digital camera, sends commands to control the digital camera, and transmits 360 the imagery to the remote computing device on the examiner side of the system. The captured image may be displayed 370 simultaneously in real-time between the local computing device and the remote computing device(s). While a single remote computing device has been generally described, it will be understood that multiple remote computing devices may receive the transmitted image.

The computing device for the operator of the microscope (slit lamp) may store software that will a) send commands to the digital camera to either be in a color or infra-red mode, b) allow capture of still or video images, and c) allow "real-time" transmission of the slit-lamp digital output over the network connection alongside face-to-face video chat to allow a remote examiner(s) to see the slit-lamp imagery as if the remote examiner was on site in the presence of the patient or facilitate collaborative patient care.

Figure 4:
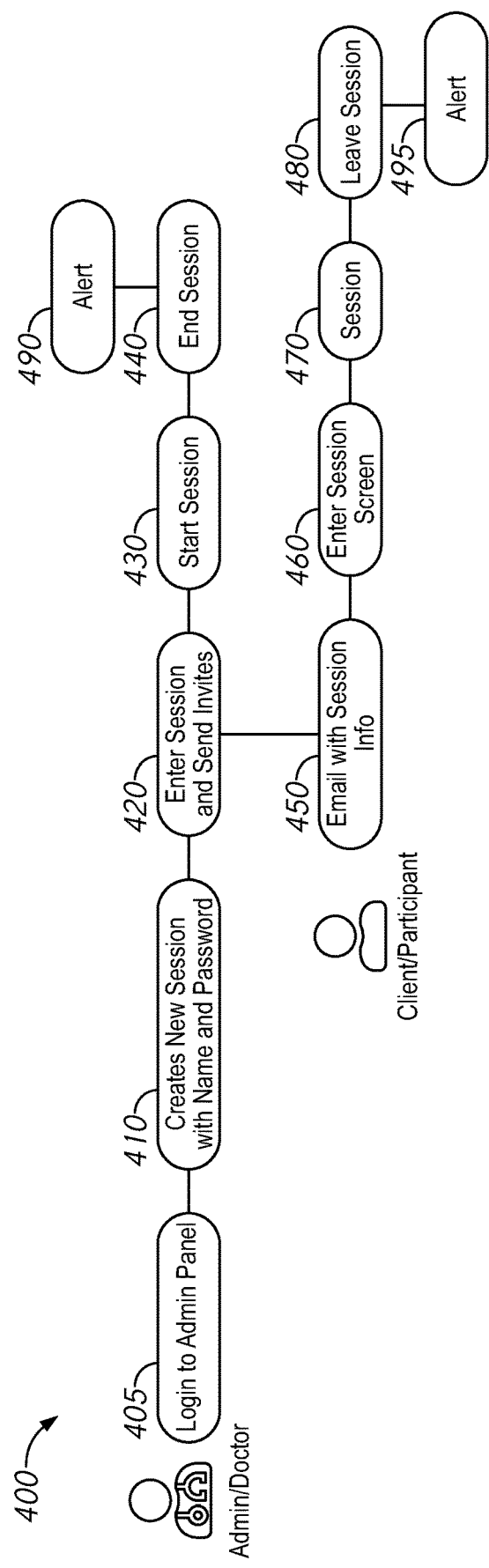
FIG. 4 is a block diagram of a process for an interactive ophthalmological online video session for remote participants in accordance with embodiments of the subject technology.

FIG. 4 shows a process 400 for an interactive ophthalmological online video session for remote participants according to an exemplary embodiment. When an administrator or physician logs in 405 to an administrative panel, a new session may be initiated 410. In an exemplary application, a physician may wish to remotely examine a patient and may wish to include multiple parties aside from the patient to the examination (for example, when desiring to show evidence to an insurance representative, seeking a second opinion from a colleague, or showing a family member the condition of the patient). The user physician may enter the session and send 420 invitations to parties (including for example, the local technician or physician's assistant and other interested third parties). In some embodiments, invitations may be sent 450 by email (or some other electronic means including for example, a notification system installed in the software application running the video session). The physician user may start 430 the video session. Third parties and the local ophthalmological device technician/operator will enter 460 the video session. The session will display 470 the captured ophthalmological imagery to the local operator and to all remote participants. The participants may engage in discussion of the examination and sharing of documents as needed. The physician/administrator user may terminate 440 the session at will and the remaining parties may leave 480 the session as needed or until it is terminated. In some embodiments, the physician user may receive an alert 490 and the invited participants may receive an alert 495 indicating the session is over.

Figure 5:
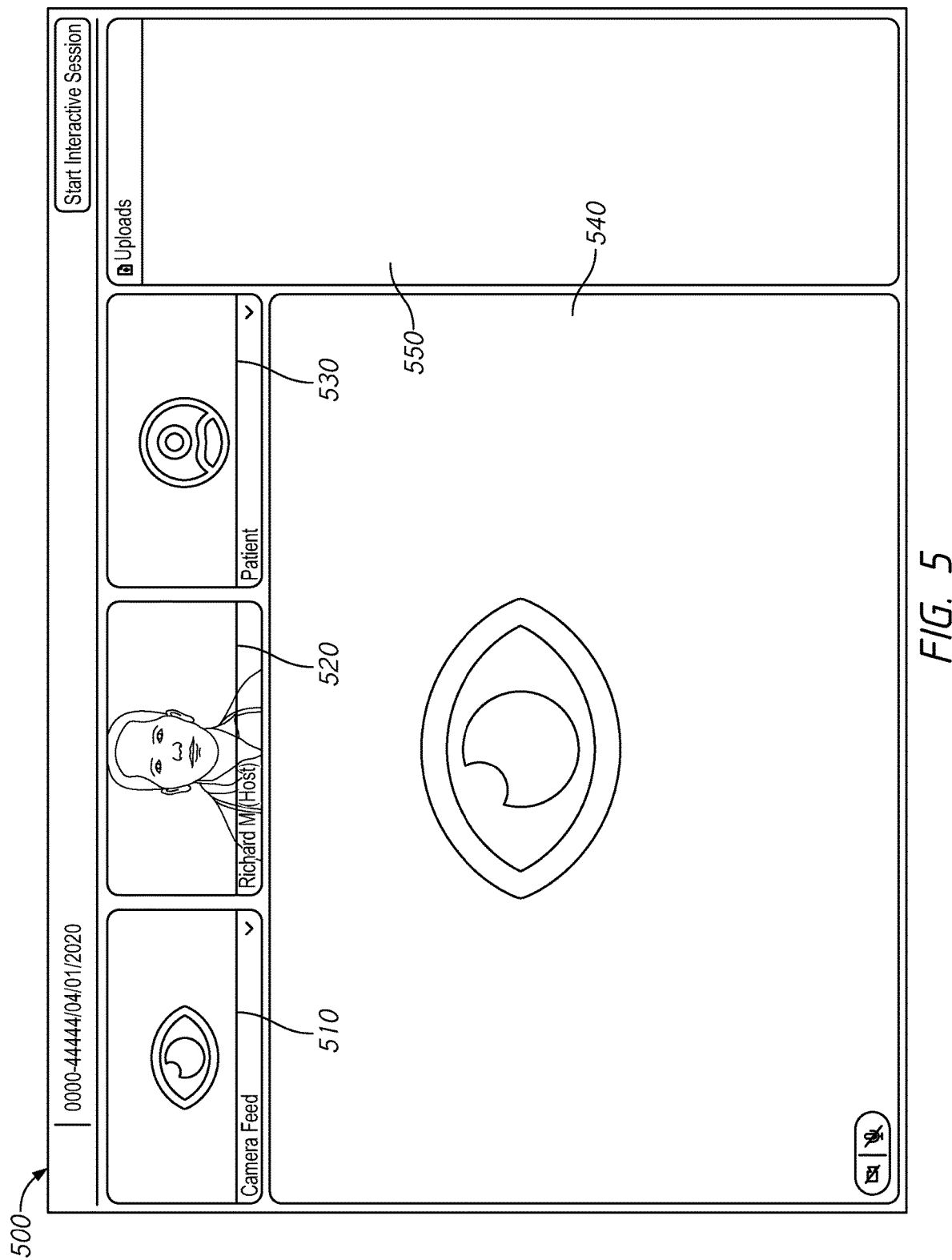
FIG. 5 is a screenshot of a user interface (UI) for an interactive ophthalmological online video session for remote participants in accordance with embodiments of the subject technology.
Figure 6:
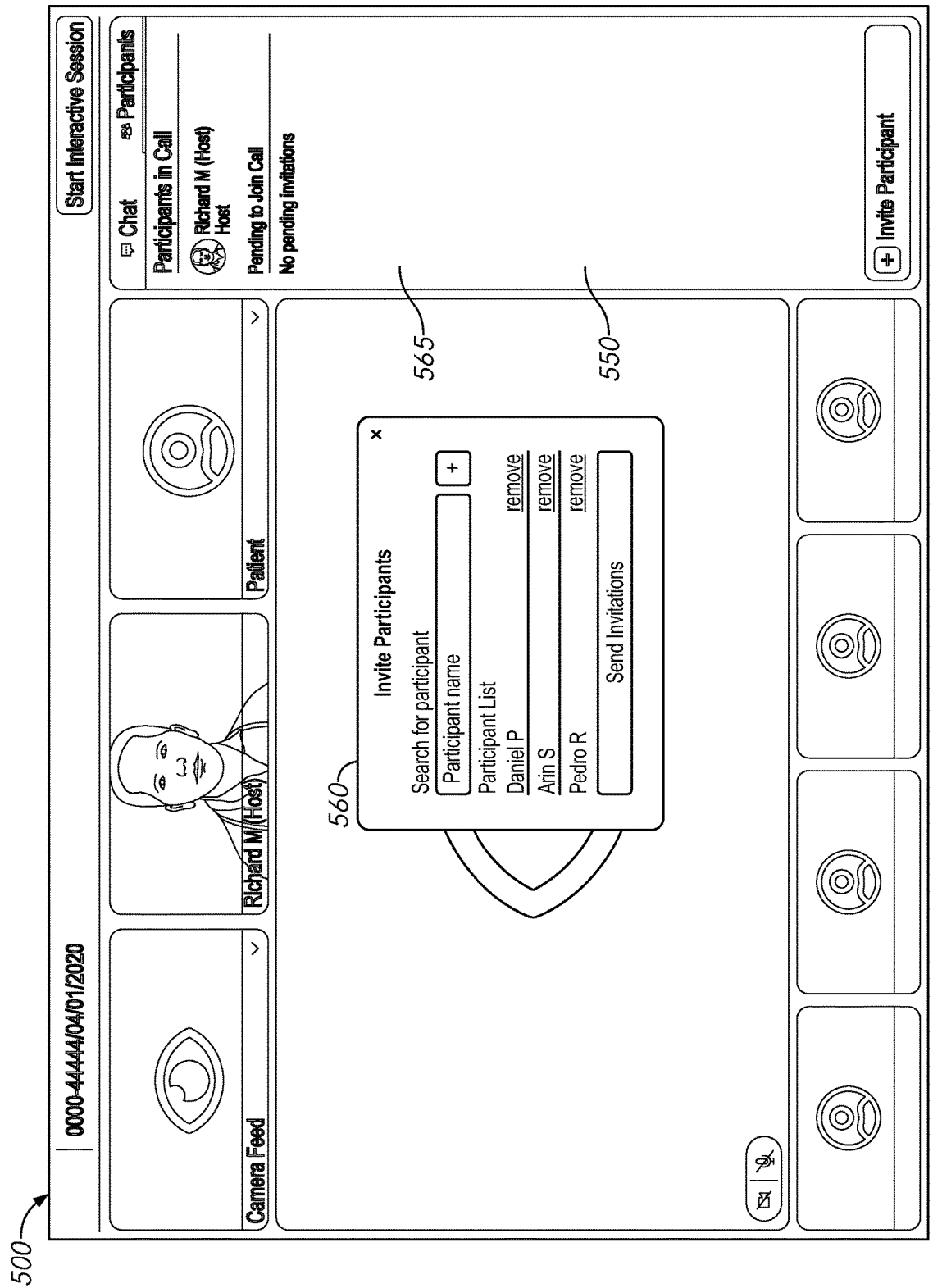
FIG. 6 is a screenshot of the UI of FIG. 5 displaying a pop-up window invitation feature in accordance with embodiments of the subject technology.
Figure 7:
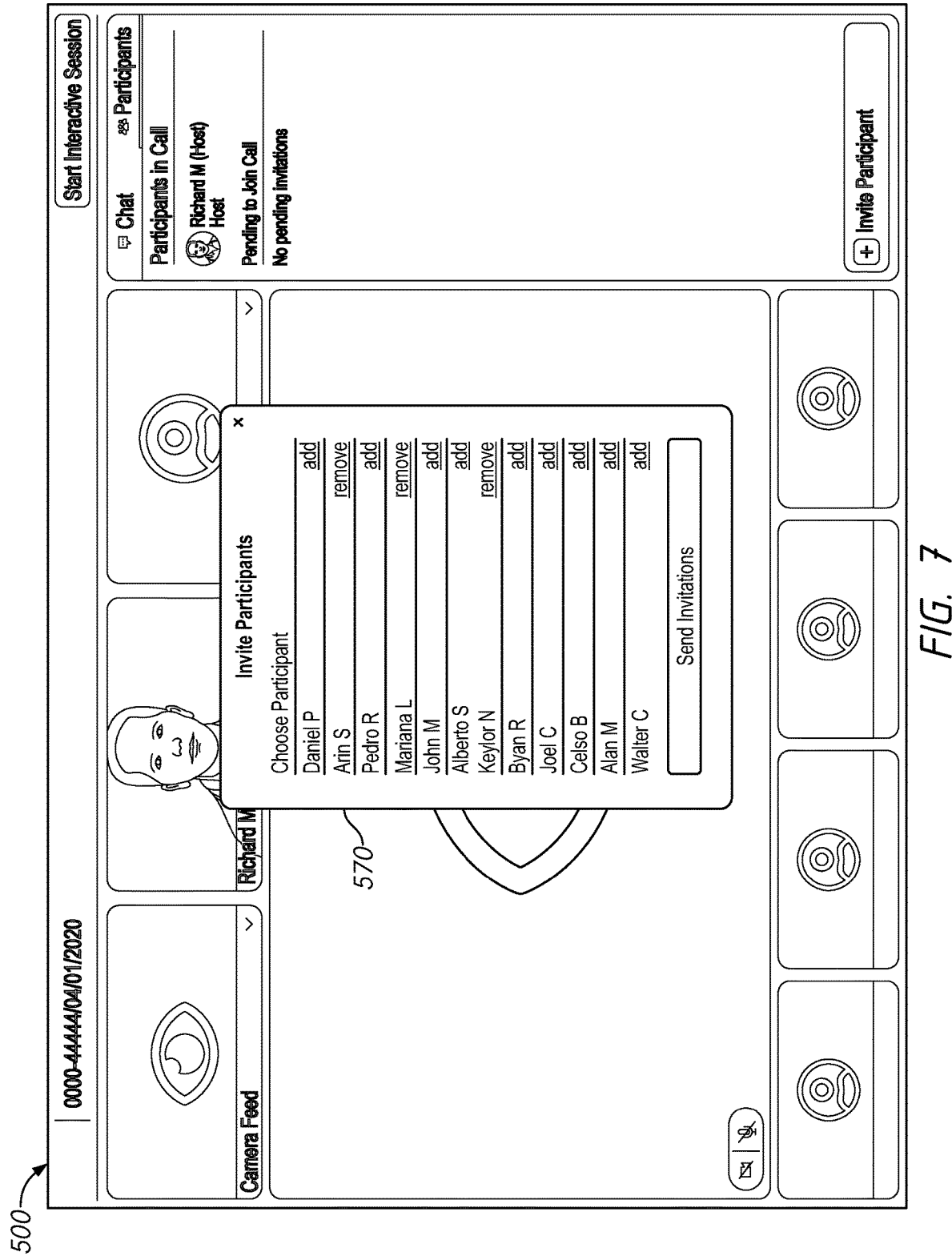
FIG. 7 is a screenshot of the UI of FIG. 5 displaying a pop-up window invitation selection menu feature in accordance with embodiments of the subject technology.
Figure 8:
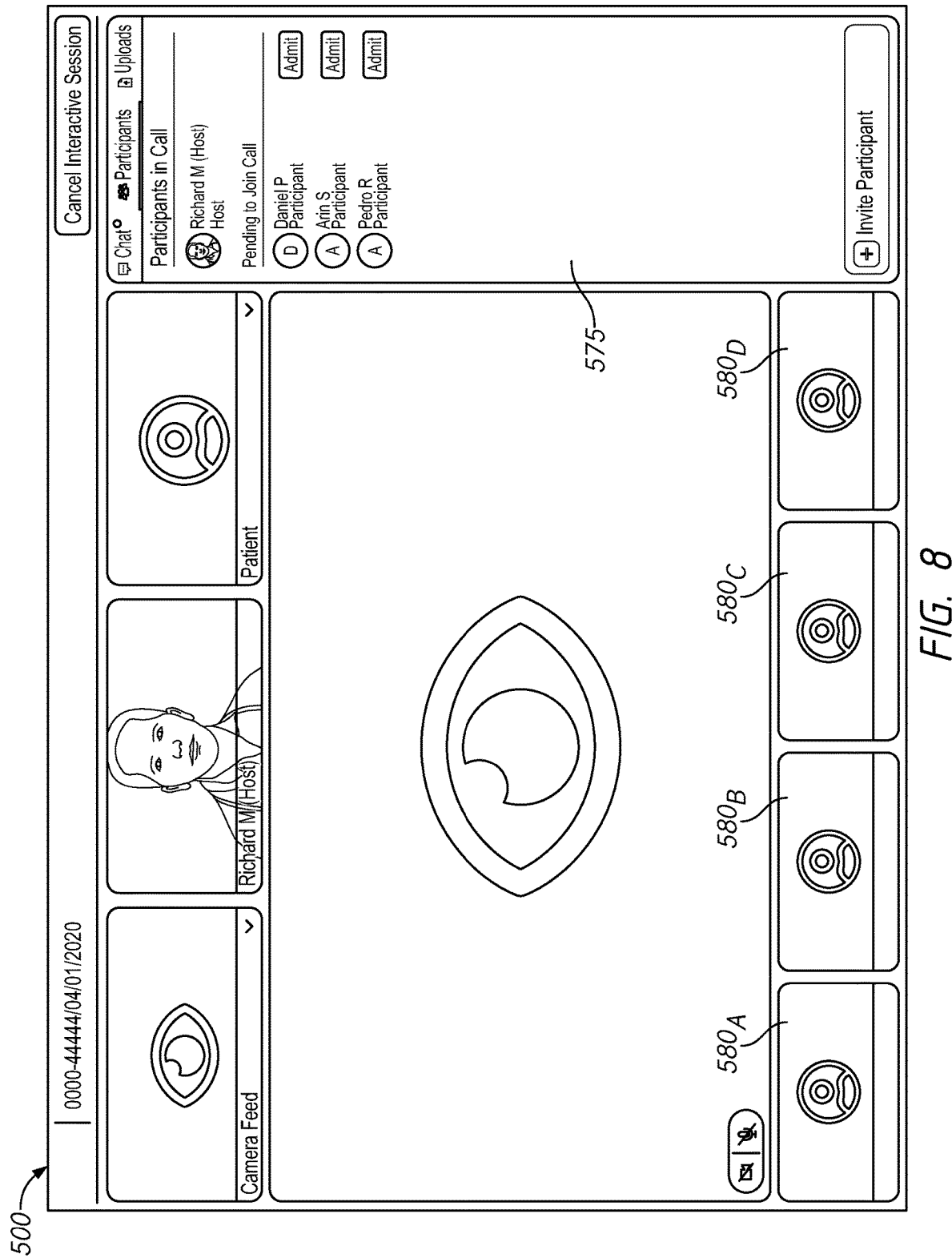
FIG. 8 is a screenshot of the UI of FIG. 5 displaying a panel of interactive participants accepting an invitation sent through the feature of FIG. 7 in accordance with embodiments of the subject technology.

FIGS. 5-16 show screenshots of a user interface (UI) 500 representing various features of a software embodiment that may be accessed via a computing device by either the physician, local ophthalmological device operator, and other third parties to view captured ophthalmological images of a patient contemporaneously taken during an examination and shown in real-time (or after the examination). In FIG. 5, the UI 500 generally includes a main panel 540 which may display different features depending on what the administrator user (generally the physician in charge of the examination) operates. Embodiments may include an auxiliary panel 550 which may be configured primarily for communication between parties engaged in an online video session. In an exemplary embodiment, the UI 500 may include a camera feed window 510, a host window 520 (which is generally displaying a photo or live picture of the physician/administrator user), and a patient window 530. The patient window 530 may show a photo of the patient during a live examination since the patient will be in front of the ophthalmological device and otherwise obscured from view. Some embodiments may include a button to initiate a live video session. FIG. 6 shows a pop-up window 560 that is configured to search a database for participants to join the video session. Temporarily referring to FIGS. 14 and 15, invitations to participants may display a status window 600 on their respective device includes a button indicating when they are ready to join and when the host is ready to conduct the video session. Participants who are pending to join or have joined the session may be displayed in the auxiliary panel 550. The displayed list of participants may be shown by selecting a participants tab 565. FIG. 7 shows a selection menu 570 that lists participants that maybe added or removed from the video session.

In some embodiments, once the video session has begun, a sub-panel of windows 580 may be displayed which show the avatars, photos, or live video of attending participants. See FIG. 8. The participant list 575 may display the names of third parties joining the video session. Window 580A may show the first participant in the list, window 580B may show the second participant, window 580C may show the third participant, and window 580D may be inactive if only three invited third parties are present.

Figure 9:
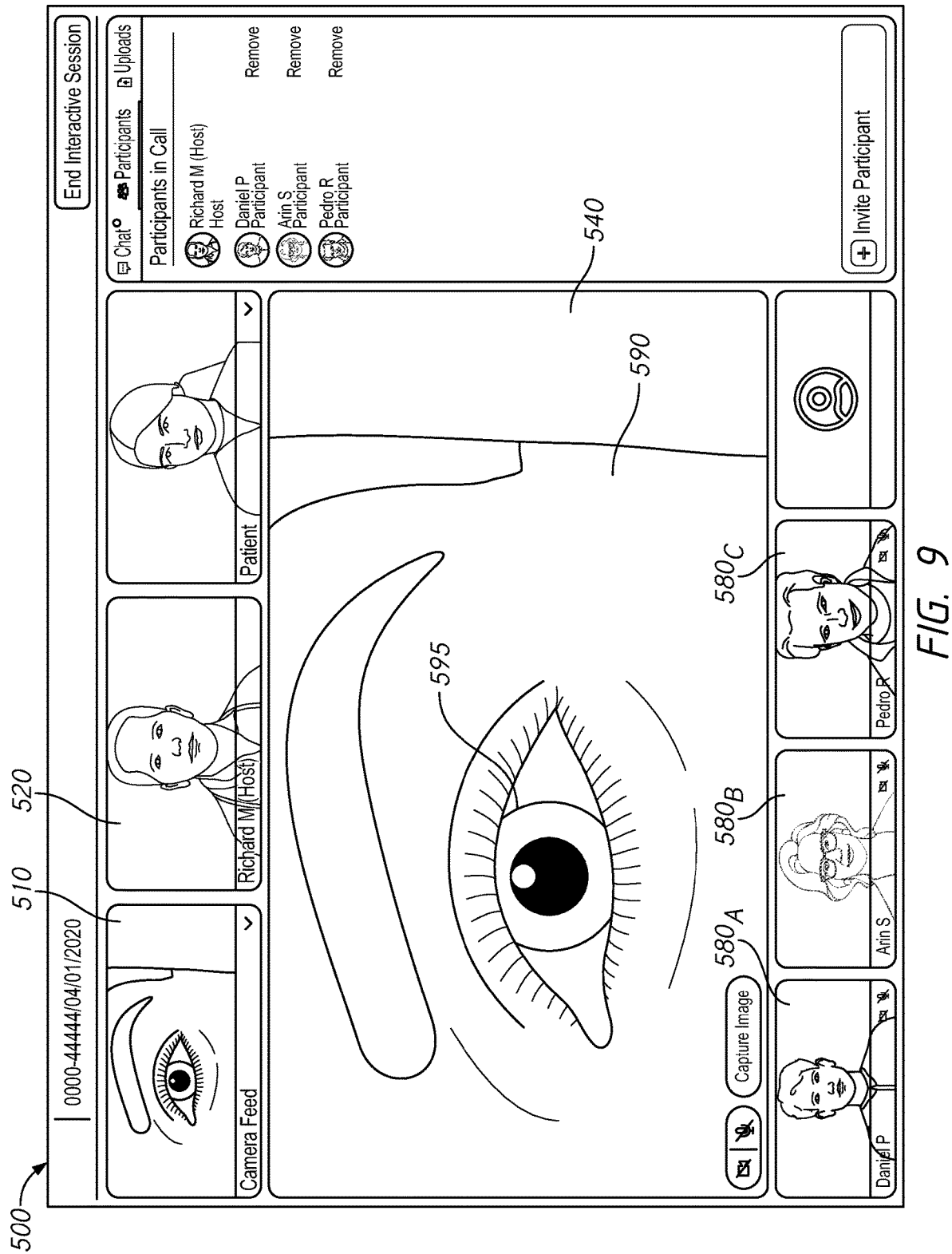
FIG. 9 is a screenshot of the UI of FIG. 5 displaying a streaming video feed of an ophthalmological image captured during a live examination in accordance with embodiments of the subject technology.
Figure 10:
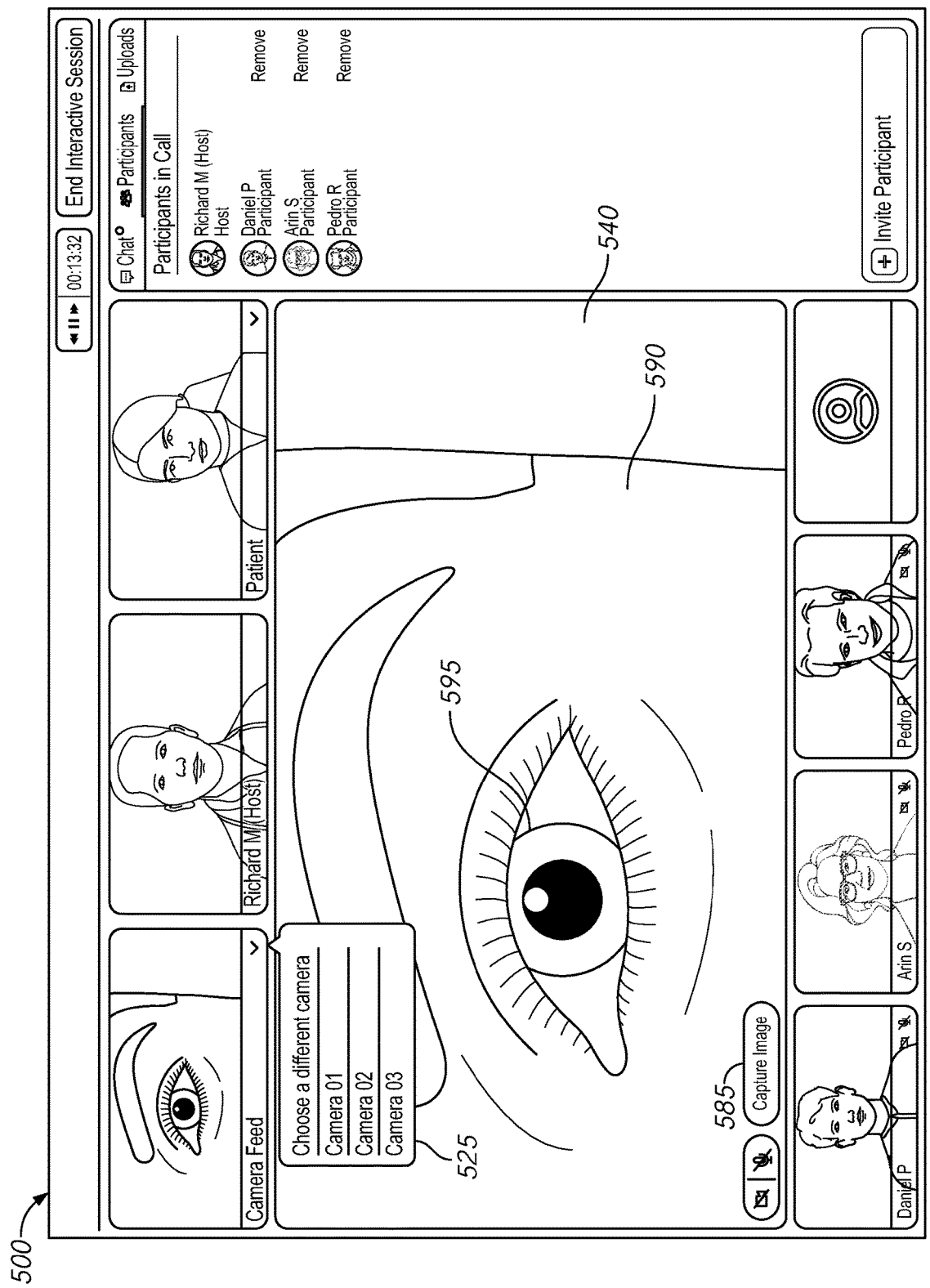
FIG. 10 is a screenshot of the UI of FIG. 9 displaying a camera selection feature in accordance with embodiments of the subject technology.

Referring now to FIGS. 9 and 10, when the ophthalmological examination system is capturing a live image 590 of the patient's eye, the user may select a view from a menu 525 in the camera feed widow 510 which may be displayed in the main panel 540 in real-time. The camera feed options available may allow the host to select a feed from the slit lamp camera, their own video camera feed, or from a camera pointing to the patient in the same room. Clicking on any of these will change the main view located in the center of the UI panel 540. The captured image may be enlarged so that the eyeball 595 and its details may be seen. Some embodiment may include a button 585 that is configured to capture a still image of the live video, which may be displayed in panel 540.

Figure 11:
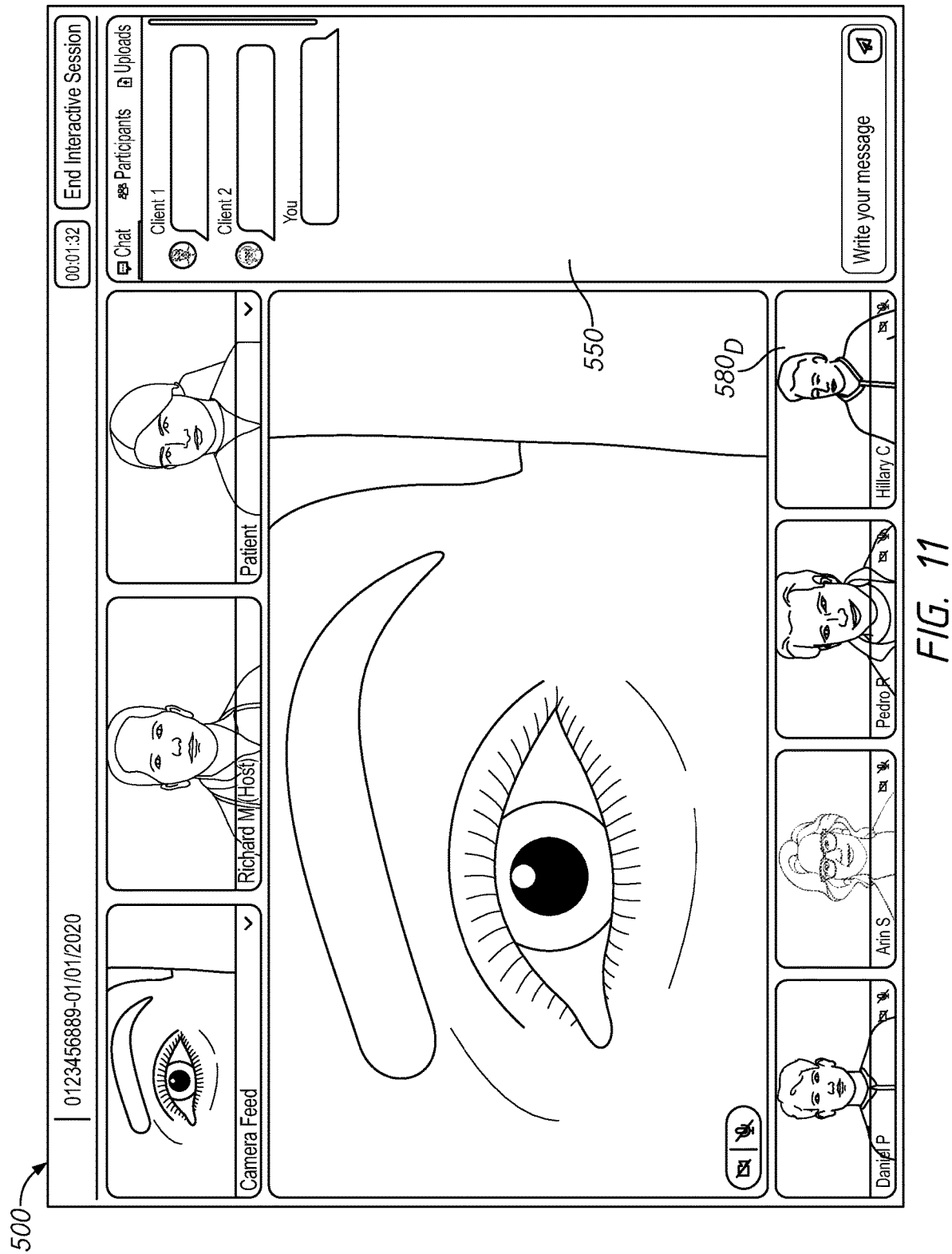
FIG. 11 is a screenshot of the UI of FIG. 9 displaying a panel for participant commentary of the captured image in accordance with embodiments of the subject technology.

Referring now to FIG. 11. some embodiments may include a chat tab that converts the panel 550 into a chat box for text entry of message by participants to comment on what is shown in the panel 540.

Figure 12:
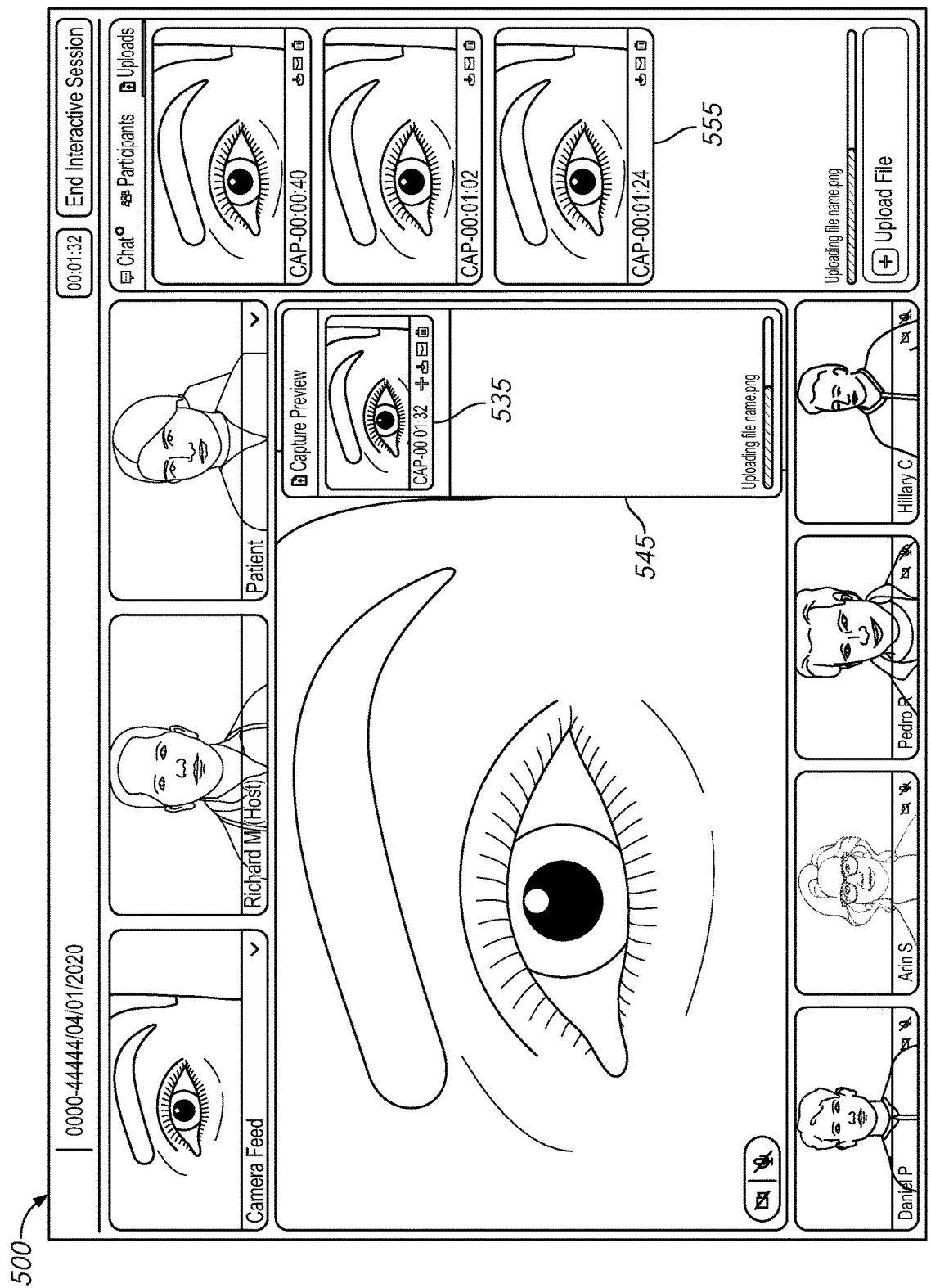
FIG. 12 is a screenshot of the UI of FIG. 9 displaying a captured image preview panel in accordance with embodiments of the subject technology.

Referring now to FIG. 12, some embodiments may include a preview pane 545 which may display still images 535 captured by the live video feed. Other embodiments may be configured to display uploaded stored images 555 in the auxiliary panel 550 by selecting an upload tab feature in the UI.

Figure 13:
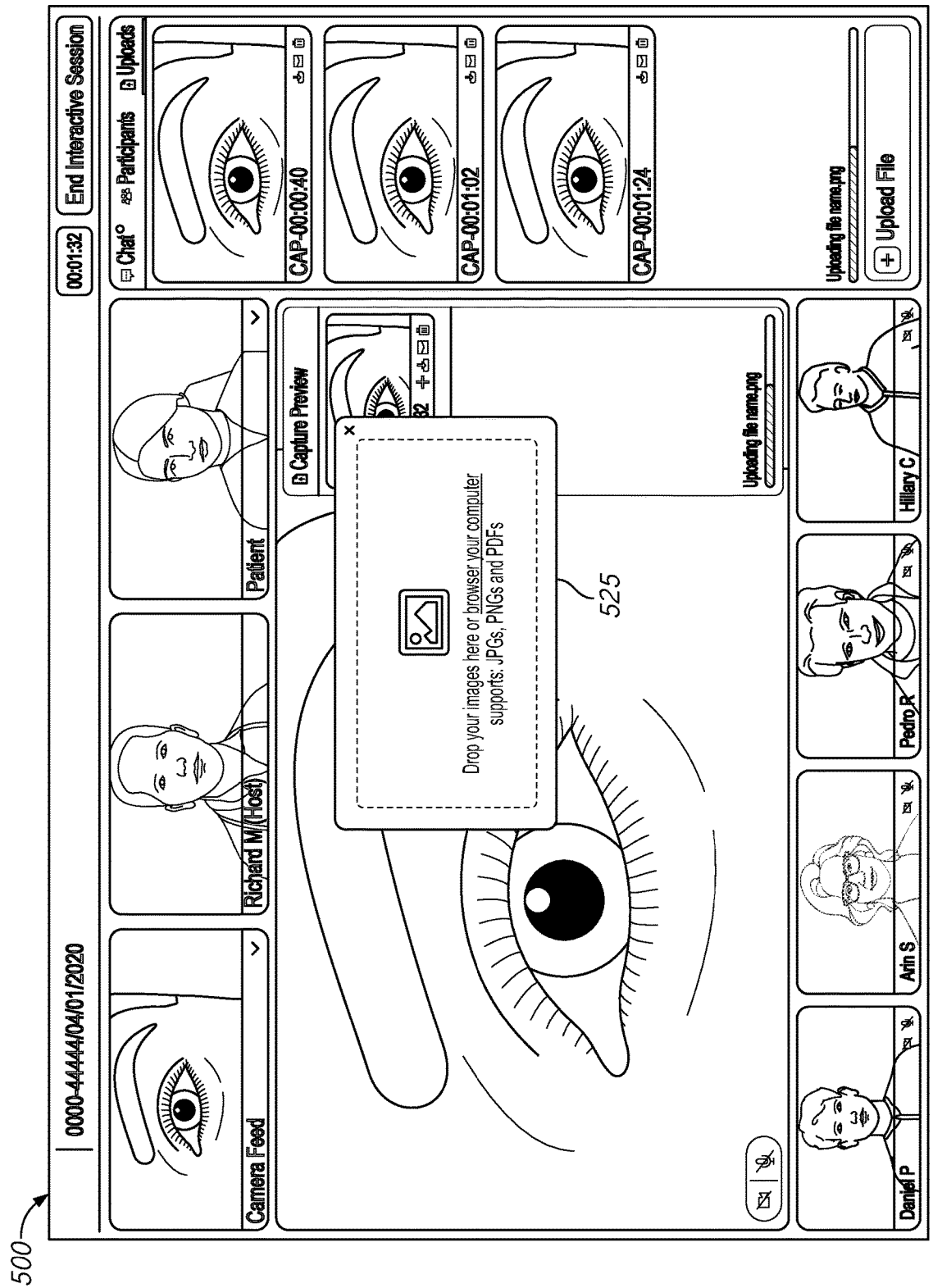
FIG. 13 is a screenshot of the UI of FIG. 12 displaying an image upload window for the captured image in accordance with embodiments of the subject technology.
Figure 14:
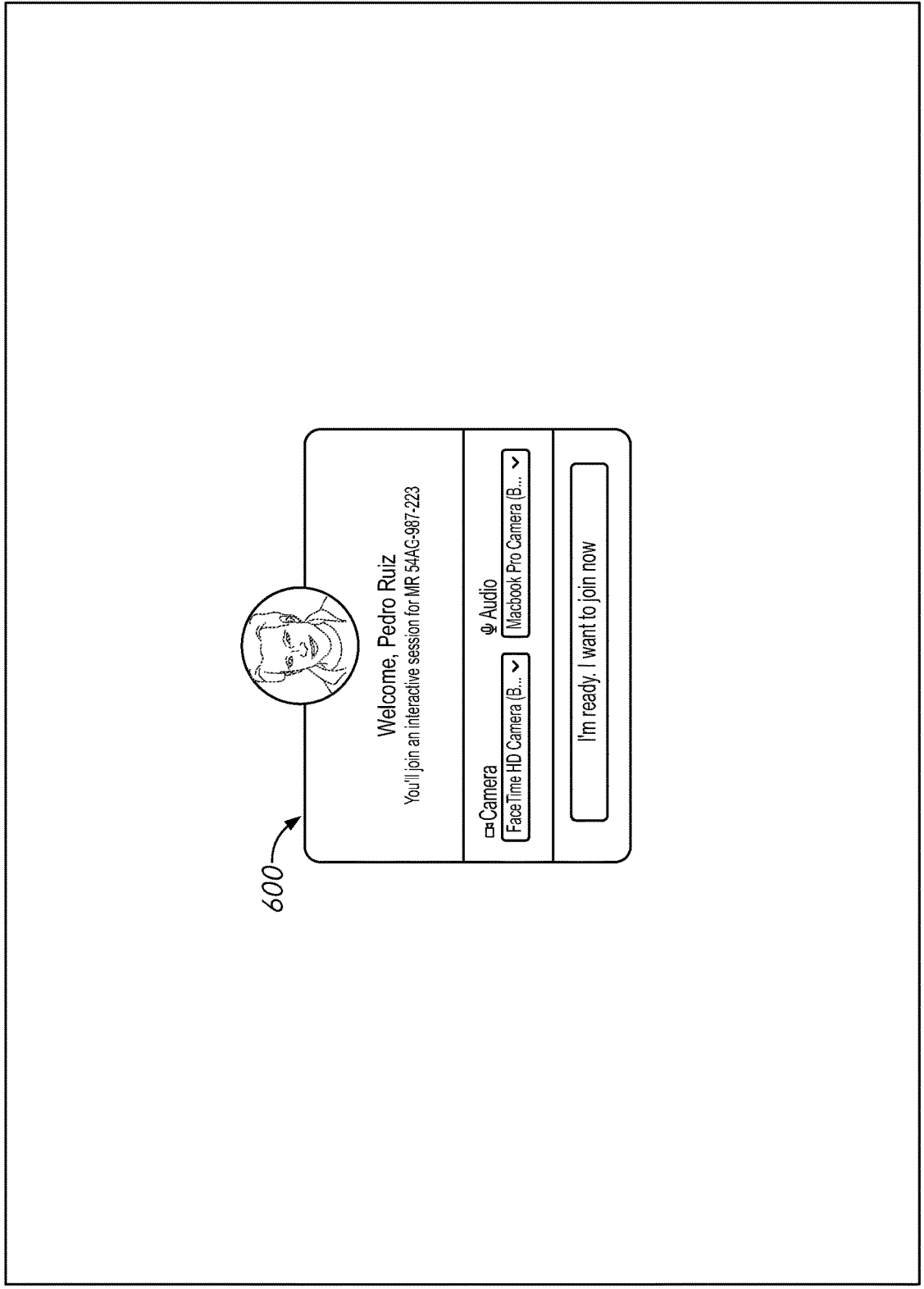
FIG. 14 is a screenshot of an online invitation UI sent to a remote participant through the system in the UI of FIG. 7 in accordance with embodiments of the subject technology.
Figure 15:
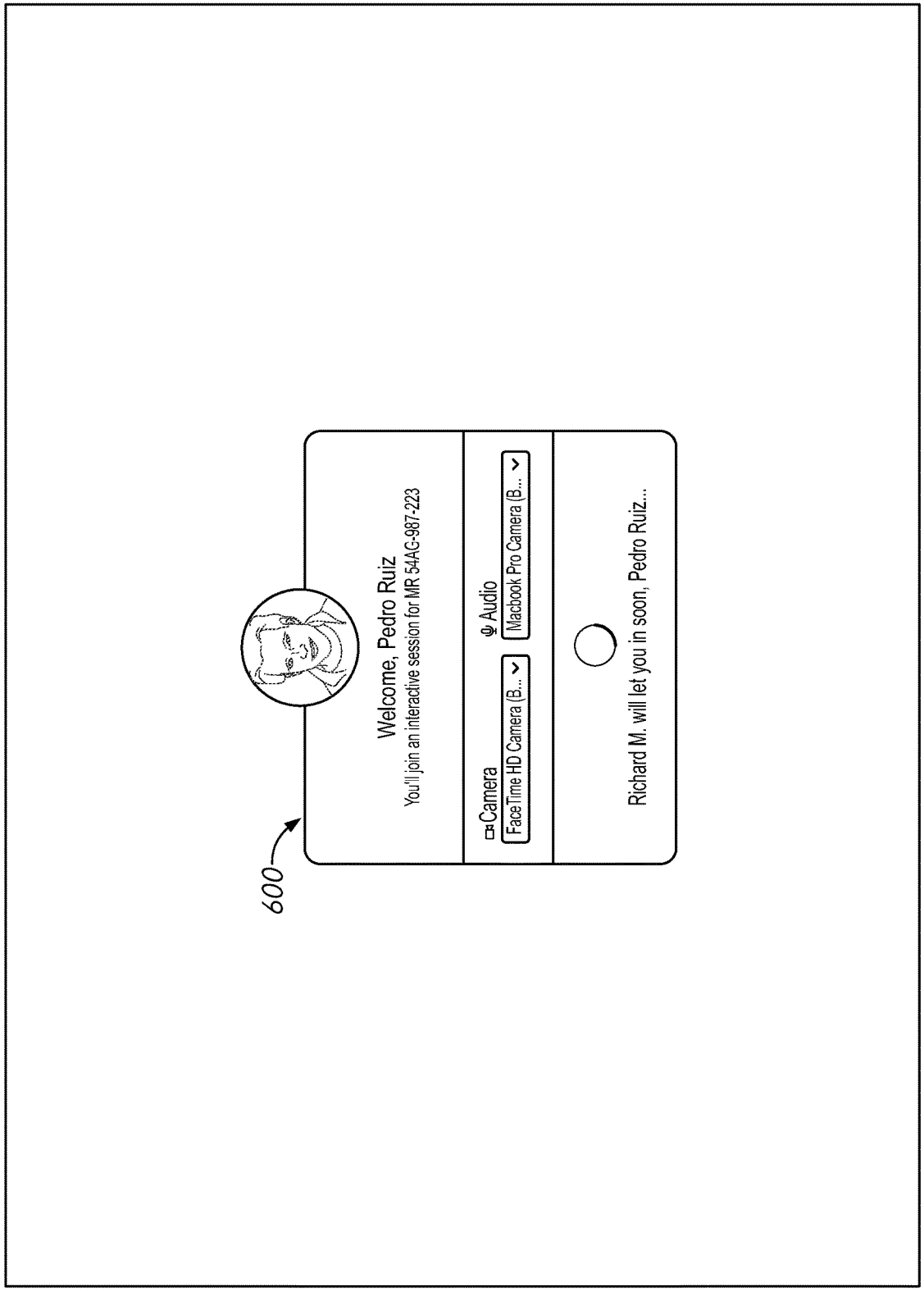
FIG. 15 is the screenshot of the UI of FIG. 14 after participant acceptance in accordance with embodiments of the subject technology.

Referring now to FIG. 13, the UI 500 may include a function to upload stored images from a computing device storage area (not shown) dropped onto an upload window 525.

Figure 16:
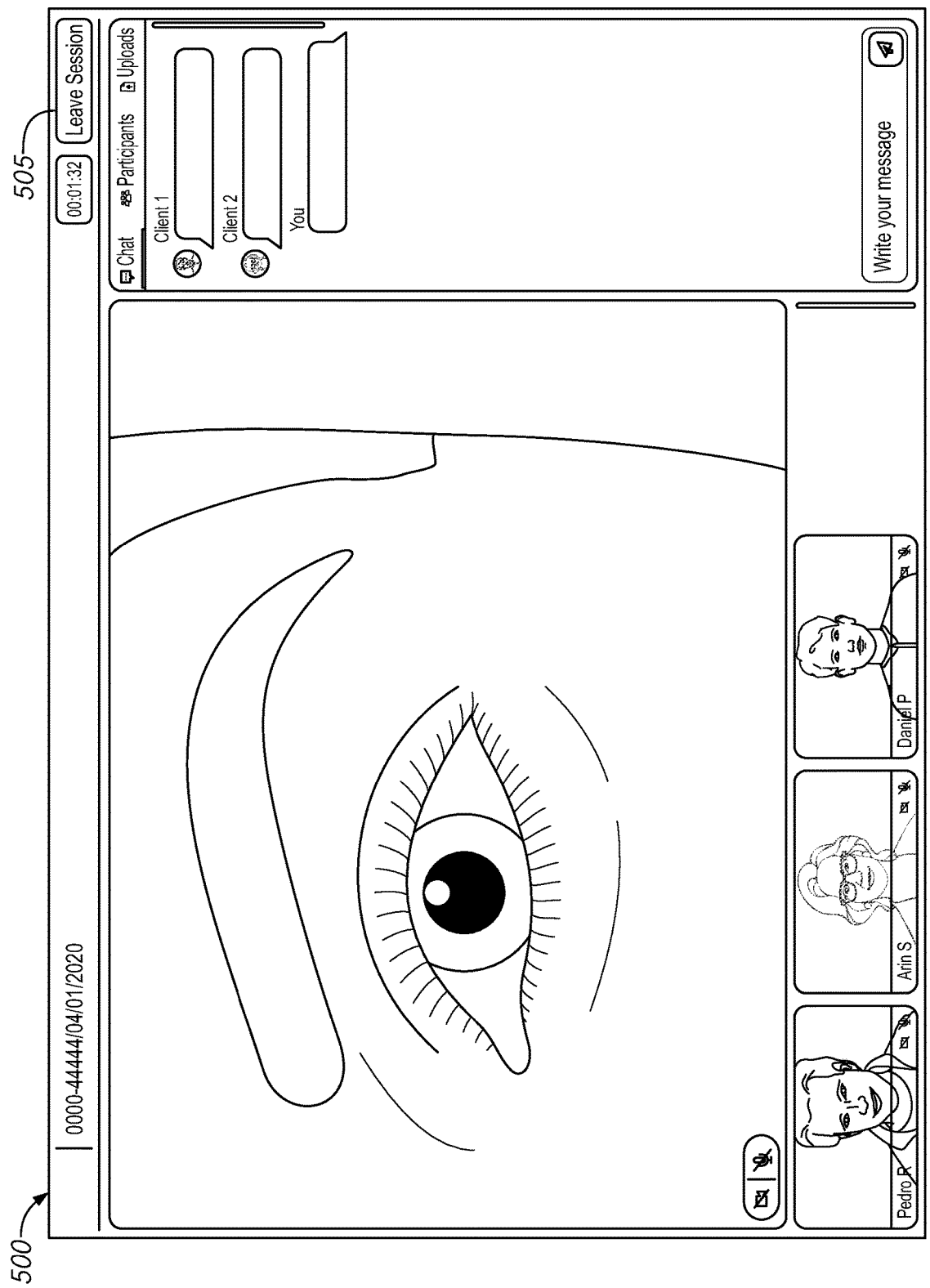
FIG. 16 is a screenshot of the UI of FIG. 9 displaying a chat panel for participant commentary of the captured image in accordance with embodiments of the subject technology.

FIG. 16 shows the UI 500 which may include a button 505 for leaving or terminating a video session.

As will be appreciated, the subject technology and accompanying software embodiments may be used with a variety of computing devices to actively participate in an ophthalmological examination. In some embodiments, the computing devices 6 and 9 (FIG. 2) may be for example, personal computer systems, tablet devices, mobile telephone devices, server computer systems, handheld or laptop devices, multiprocessor systems, microprocessor-based systems, set top boxes, programmable consumer electronics, network PCs, and distributed cloud computing environments that include any of the above systems or devices, and the like. The computing devices 6 and 9 may be described in the general context of computer system executable instructions, such as program modules, being executed by a computer system. In some embodiments, the computing devices 6 and 9 may be connected through a computer-based network and may be practiced in distributed cloud computing environments where tasks are performed by remote processing devices that are linked through a communications network. In a distributed cloud computing environment, program modules may be located in both local and remote computer system storage media including memory storage devices.

The computing devices 6 and 9 may include at least one program product having a set of program modules that are configured to carry out the functions of embodiments of the invention. The program modules generally carry out the functions and/or methodologies of embodiments of the invention as described herein.

Aspects of the disclosed invention may be embodied as a system, method or process, or computer program product (sometimes called a software application). Accordingly, aspects of the disclosed invention may take the form of an entirely hardware embodiment, an entirely software embodiment (including firmware, resident software, micro-code, etc.) or an embodiment combining software and hardware aspects "system." Furthermore, aspects of the disclosed invention may take the form of a computer program product embodied in one or more computer readable media having computer readable program code embodied thereon.

Aspects of the disclosed invention are described above with reference to block diagrams of methods, apparatus (systems) and computer program products according to embodiments of the invention. It will be understood that each block of the block diagrams, and combinations of blocks in the flowchart illustrations and/or block diagrams, can be implemented by computer program instructions. These computer program instructions may be provided to the processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above. While some details of the accompanying figures are not described above, their use and configuration are understood by those of ordinary skill in the art and are part of the disclosure herein.

What is claimed is:

1. An ophthalmic system for tele-ophthalmology and collaborative care, comprising:
    a slit lamp configured to capture an image of an eye of a patient;
    a digital camera coupled to the slit lamp and positioned to capture imagery from the light output of a beam splitter;
    a video adapter coupled to the slit lamp to focus a light output from the slit lamp to the attached digital camera;
    a communications cable connected between the digital camera and a first computing device, to forward the captured imagery to the first computing device;
    a network connection configured to transmit the captured imagery from the first computing device to a remote computing device(s) connected wirelessly to the first computing device, wherein the transmitted captured imagery is seen in real-time as if remote user(s) at the remote computing device(s) were seeing the image of the eye of the patient on site in the presence of the patient;
    wherein the network connection is configured to transmit the captured imagery alongside a face-to-face audio-visual communication; and
    wherein the computer network connection is further configured to provide a camera feed function wherein a camera feed view is switchable between a perspective of either the slit lamp, a user's computing device camera, or an auxiliary camera in a room and pointing at the patient.

2. The ophthalmic system of claim 1, further comprising a beam splitter coupled to the slit lamp and disposed to partially divert the light output from the slit lamp to the first computing device, wherein the image of the eye of the patient is viewable simultaneously through the slit lamp, by a display in the first computing device, and by displays in the remote computing device(s).

3. The ophthalmic system of claim 1, further comprising a computer program product comprising a non-transitory computer readable storage medium having computer readable program code embodied therewith, the computer readable program code being configured to, when executed by a processor in either the first computing device and/or the remote computing device(s) convert the captured imagery in the digital camera into a data format compatible with web streaming in real-time and forward the converted captured imagery from the first computing device to the remote computing device(s) for display as a live video session.

4. The ophthalmic system of claim 3, wherein the computer readable program code is further configured to host a video conference between remote participants while displaying the captured imagery in real-time, wherein the patient and the slit lamp are in a first location and the remote participants are in a second location, remote from the first location.

5. A method of performing a tele-ophthalmological examination on a patient, comprising:
    capturing light reflected off a patient's eye using a slit lamp in a first location, wherein the slit lamp is coupled to a video adapter configured to focus a light output from the slit lamp;
    splitting the reflected light from the patient's eye in the slit lamp;
    diverting a portion of the split reflected light into a digital camera, wherein the video adapter coupled to the slit lamp focuses the light output from the slit lamp to the digital camera;
    converting the reflected light diverted to the digital camera into a digital format of data;
    transmitting the digitally formatted data through a network to a remote computing device located in a second location;
    displaying an image of the patient's eye in real-time video on the remote computing device;
    displaying the image alongside a face-to-face audio-visual communication; and
    providing a camera feed function wherein a camera feed view is switchable between a perspective of either the slit lamp, a user's computing device camera, or an auxiliary camera in a room and pointing at the patient.

6. The method of claim 5, further comprising displaying the image of the patient's eye on a local computing device coupled to the slit lamp, wherein the display of the patient's eye on the local computing device and on the remote computing device occurs simultaneously.

7. The method of claim 5, further comprising:
    hosting a live video session on the remote computing device;
    inviting at least one third party participant to join the live video session from another computing device that is remote from the remote computing device; and
    displaying the real-time video of the image of the patient's eye to the invited third party participant through the live video session.

8. The method of claim 7, further comprising:
    providing a still image capture function, wherein a still image of the real-time video is captured during the live video session; and
    providing an upload function wherein the captured still image is displayed to all the members of the live video session.

9. The method of claim 7, further comprising providing a chat panel, wherein a host of the live video session and the third party participant may communicate by chatting in the chat panel.

10. A computer program product for hosting tele-ophthalmological examination comprising a non-transitory computer readable storage medium having computer readable program code embodied therewith, the computer readable program code being configured to, when executed by a processor:
  capture light reflected off a patient's eye using a slit lamp in a first location;
  split the reflected light from the patient's eye in the slit lamp;
  use a video adapter coupled to the slit lamp to focus a light output from the slit lamp to divert a portion of the split reflected light into a digital camera;
  convert the reflected light diverted to the digital camera into a digital format of data;
  transmit the digitally formatted data through a network to a remote computing device located in a second location;
  display an image of the patient's eye in real-time video on the remote computing device;
  display the image alongside a face-to-face audio-visual communication; and
  provide a camera feed function wherein a camera feed view is switchable between a perspective of either the slit lamp, a user's computing device camera, or an auxiliary camera in a room and pointing at the patient.

11. The computer program product of claim 10, wherein the computer readable program code is further configured to display the image of the patient's eye on a local computing device coupled to the slit lamp, wherein the display of the patient's eye on the local computing device and on the remote computing device occurs simultaneously.

12. The computer program product of claim 10, wherein the computer readable program code is further configured to:
  host a live video session on the remote computing device;
  invite at least one third party participant to join the live video session from another computing device that is remote from the remote computing device; and
  display the real-time video of the image of the patient's eye to the invited third party participant through the live video session.

13. The computer program product of claim 12, wherein the computer readable program code is further configured to:
  provide a still image capture function, wherein a still image of the real-time video is captured during the live video session; and
  provide an upload function wherein the captured still image is displayed to all the members of the live video session.

14. The computer program product of claim 12, wherein the computer readable program code is further configured to provide a chat panel, wherein a host of the live video session and the third party participant may communicate by chatting in the chat panel.

15. The ophthalmic system of claim 4 wherein the digital slit-lamp is interfaced with a web-based software platform configured to allow an observer to view the slit-lamp examination imagery being conducted at a remote location in real-time seamlessly and alongside "face-to-face" video chat.

16. The ophthalmic system of claim 15 wherein the web-based software platform comprises WebRTC.

17. The method of claim 7 wherein the digital slit-lamp is interfaced with a web-based software platform configured to allow an observer to view the slit-lamp examination imagery being conducted at a remote location in real-time seamlessly and alongside "face-to-face" video chat.

18. The method of claim 16 wherein the web-based software platform comprises WebRTC.

19. The computer program product of claim 12 wherein the digital slit-lamp is interfaced with a web-based software platform configured to allow an observer to view the slit-lamp examination imagery being conducted at a remote location in real-time seamlessly and alongside "face-to-face" video chat.

20. The computer program product of claim 19 wherein the web-based software platform comprises WebRTC.

* * * * *